US011419963B2

(12) United States Patent
Kawarabayashi et al.

(10) Patent No.: US 11,419,963 B2
(45) Date of Patent: Aug. 23, 2022

(54) BLOOD PURIFICATION APPARATUS

(71) Applicant: Nikkiso Company Limited, Tokyo (JP)

(72) Inventors: Satoru Kawarabayashi, Tokyo (JP);
Shinya Hasegawa, Shizuoka (JP);
Tomoya Murakami, Shizuoka (JP);
Kunihiko Akita, Shizuoka (JP);
Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 191 days.

(21) Appl. No.: 16/845,285

(22) Filed: Apr. 10, 2020

(65) Prior Publication Data

US 2020/0237988 A1    Jul. 30, 2020

Related U.S. Application Data

(63) Continuation of application No. PCT/JP2018/038713, filed on Oct. 17, 2018.

(51) Int. Cl.
*A61M 1/16* (2006.01)
*G01N 33/50* (2006.01)
(Continued)

(52) U.S. Cl.
CPC ........ *A61M 1/1603* (2014.02); *A61M 1/1656* (2013.01); *A61M 1/267* (2014.02);
(Continued)

(58) Field of Classification Search
CPC .............. A61M 1/1603; A61M 1/1609; A61M 1/1615; A61M 1/1656; A61M 1/267;
(Continued)

(56) References Cited

U.S. PATENT DOCUMENTS

| | | |
|---|---|---|
| 6,702,774 B1 | 3/2004 | Polaschegg |
| 2006/0116624 A1 | 6/2006 | Sternby |
| 2010/0112583 A1 | 5/2010 | Ichiishi et al. |

FOREIGN PATENT DOCUMENTS

| | | |
|---|---|---|
| EP | 3042672 A1 | 7/2016 |
| JP | H03-173569 A | 7/1991 |

(Continued)

OTHER PUBLICATIONS

Yamashita, "Basics of Blood Purification", "The Japanese Journal of Clinical Dialysis", vol. 15, No. 11, pp. 75-79, 1999.

(Continued)

*Primary Examiner* — Dirk R Bass
(74) *Attorney, Agent, or Firm* — Young Basile Hanlon & MacFarlane, P.C.

(57) ABSTRACT

A blood purification apparatus with a blood circuit that allows a patient's blood to extracorporeally circulate and a blood purifier connected to the blood circuit and that purifies the blood in extracorporeal circulation are attachable, the blood purification apparatus including a dialysate introduction line through which dialysate is introduced into the blood purifier; a dialysate drain line through which waste dialysate resulting from blood purification performed by the blood purifier is drained from the blood purifier; and a concentration-detecting unit that detects a concentration of a predetermined substance in the waste dialysate flowing through the dialysate drain line. The blood purification apparatus includes a control unit that establishes a state of equilibrium where the concentration of the predetermined substance in the waste dialysate flowing through the dialysate drain line and a concentration of the predetermined substance in the blood flowing through the blood circuit are equal or approximate to each other; a storage unit that stores a value detected by the concentration-detecting unit in the state of equilibrium as an equilibrium value; and a clear-space-calculating
(Continued)

unit that calculates clear space in accordance with the value detected by the concentration-detecting unit and the equilibrium value stored in the storage unit, the clear space being an index representing a volume of purification of a patient achieved by blood purification treatment.

9 Claims, 6 Drawing Sheets

(51) Int. Cl.
    *A61M 1/36*     (2006.01)
    *A61M 1/26*     (2006.01)

(52) U.S. Cl.
    CPC ....... *A61M 1/3638* (2014.02); *G01N 33/5005* (2013.01); *A61M 2205/3306* (2013.01); *A61M 2205/3334* (2013.01); *A61M 2205/3389* (2013.01); *A61M 2205/52* (2013.01)

(58) Field of Classification Search
    CPC .............. A61M 1/3612; A61M 1/3638; A61M 2202/0498; A61M 2205/3306; A61M 2205/3334; A61M 2205/3389; A61M 2205/50; A61M 2205/52; G01N 33/5005
    See application file for complete search history.

(56) References Cited

FOREIGN PATENT DOCUMENTS

| | | |
|---|---|---|
| JP | 2007-029705 A | 2/2007 |
| JP | 2010252962 A | 11/2010 |
| WO | 2016/016039 A1 | 2/2016 |

OTHER PUBLICATIONS

European Search Report for Application No. 18868007.8, dated Jun. 28, 2021.

BLOOD PURIFICATION APPARATUS

CROSS-REFERENCE TO RELATED APPLICATION(S)

This application is a continuation of International Application No. PCT/JP2018/038713, filed on Oct. 17, 2018, which claims priority to Japanese Application No. 2017-201428, filed on Oct. 17, 2017, the entire disclosures of which are hereby incorporated by reference.

FIELD

The present invention relates to a blood purification apparatus that calculates clear space as an index representing the volume of purification of a patient achieved by blood purification treatment.

BACKGROUND

Hemodialysis treatment is a kind of blood treatment of purifying a patient's blood while causing the blood to extracorporeally circulate. In hemodialysis treatment, a dialyzer as a blood purifier through which dialysate is allowed to flow is used, and a blood circuit through which the patient's blood is caused to extracorporeally circulate is connected to the dialyzer. The blood and the dialysate are brought into contact with each other through semipermeable membranes provided in the dialyzer, whereby waste matter in the blood or excessive water is removed (the removal of excessive water is referred to as "ultrafiltration"). The blood purified by the dialyzer is returned to the patient's body through a puncture needle. Meanwhile, the waste matter or the excessive water is drained to the outside together with the dialysate through a dialysate drain line.

Appropriately evaluating and grasping the volume of purification of the patient achieved by blood purification treatment is important in giving appropriate treatment. One of indices that represent the volume of purification of the patient achieved by the blood purification treatment is clear space (CS). As disclosed by NPL 1, for example, clear space (CS) is obtained by calculating the volume of urea removal as follows. Waste dialysate resulting from the blood purification treatment and drained from the blood purifier (the dialyzer) is all stored, and the concentration of urea in the stored waste dialysate is detected.

Citation List. NPL 1: "Basics of Blood Purification", "The Japanese Journal of Clinical Dialysis", 1999, Vol. 15, No. 11, pp. 75-79, Akihiro Yamashita, the teachings of which are expressly incorporated by reference herein for all purposes.

SUMMARY

However, the above known blood purification method has a problem in that since the waste dialysate resulting from the blood purification treatment and drained from the blood purifier needs to be all stored, a tank or the like for storing all the waste dialysate is necessary. Such a situation increases the size of the apparatus and disables real-time calculation of clear space.

The present invention has been conceived in view of the above circumstances and provides a blood purification apparatus capable of calculating clear space in real time while avoiding the size increase of the apparatus.

According to the teachings herein, there is provided a blood purification apparatus to which a blood circuit that allows a patient's blood to extracorporeally circulate and a blood purifier connected to the blood circuit and that purifies the blood in extracorporeal circulation are attachable, the blood purification apparatus including a dialysate introduction line through which dialysate is introduced into the blood purifier; a dialysate drain line through which waste dialysate resulting from blood purification performed by the blood purifier is drained from the blood purifier; and a concentration-detecting unit that detects a concentration of a predetermined substance in the waste dialysate flowing through the dialysate drain line. The blood purification apparatus includes a control unit that establishes a state of equilibrium where the concentration of the predetermined substance in the waste dialysate flowing through the dialysate drain line and a concentration of the predetermined substance in the blood flowing through the blood circuit are equal or approximate to each other; a storage unit that stores a value detected by the concentration-detecting unit in the state of equilibrium as an equilibrium value; and a clear-space-calculating unit that calculates clear space in accordance with the value detected by the concentration-detecting unit and the equilibrium value stored in the storage unit, the clear space being an index representing a volume of purification of a patient achieved by blood purification treatment.

According to the teachings herein, in the blood purification apparatus taught herein, the clear-space-calculating unit calculates clear space through the following mathematical expression:

$$CS = \frac{1}{C_{deq(0)}} \int_0^{te} C_d(t) \cdot Q_d(t) dt \qquad [\text{Math. 1}]$$

(where CS denotes clear space, Cdeq denotes the equilibrium value stored in the storage unit, Cd(t) denotes the concentration of the predetermined substance detected by the concentration-detecting unit, Qd(t) denotes dialysate flow rate, t denotes arbitrary time in the blood purification treatment, and te denotes end time of the blood purification treatment).

According to the teachings herein, in the blood purification apparatus taught herein, the control unit establishes the state of equilibrium by reducing or stopping the dialysate flow rate, increasing the blood flow rate, or causing the dialysate to circulate through the blood purifier.

According to the teachings herein, in the blood purification apparatus taught herein, the concentration-detecting unit includes a light-emitting portion that emits light toward the waste dialysate, a light-receiving portion that receives the light emitted from the light-emitting portion and transmitted through the waste dialysate, and a detecting portion that detects absorbance in accordance with an intensity of the light received by the light-receiving portion, the concentration-detecting unit detecting the concentration of the predetermined substance in the waste dialysate in accordance with the absorbance detected by the detecting portion.

According to the teachings herein, in the blood purification apparatus taught herein, the storage unit stores, as the equilibrium value, the absorbance detected by the detecting portion in the state of equilibrium, and the clear-space-calculating unit calculates clear space in accordance with the absorbance detected by the detecting portion and the equilibrium value stored in the storage unit.

According to the taught herein, in the blood purification apparatus taught herein, the clear-space-calculating unit calculates clear space through the following mathematical expression:

$$CS = \frac{1}{\text{Abs}_{eq(0)}} \int_0^{te} \text{Abs}(t) \cdot Q_d(t) dt \qquad [\text{Math. 2}]$$

(where CS denotes clear space, Abs denotes the absorbance detected by the detecting portion, Abseq denotes the equilibrium value stored in the storage unit, Qd(t) denotes dialysate flow rate, t denotes arbitrary time in the blood purification treatment, and te denotes end time of the blood purification treatment).

According to the teachings herein, the blood purification apparatus taught herein further includes a total-body-fluid-volume-calculating unit that calculates the patient's total body-fluid volume in accordance with the clear space calculated by the clear-space-calculating unit.

According to the teachings herein, the blood circuit and the blood purifier are attached to the blood purification apparatus taught herein.

According to the teachings herein, a state of equilibrium is established where the concentration of the predetermined substance in the waste dialysate flowing through the dialysate drain line and the concentration of the predetermined substance in the blood flowing through the blood circuit are equal or approximate to each other. Furthermore, the value detected by the concentration-detecting unit in the state of equilibrium is stored as an equilibrium value. Furthermore, clear space as an index representing the volume of purification of the patient achieved by the blood purification treatment is calculated in accordance with the value detected by the concentration-detecting unit and the equilibrium value stored in the storage unit. Therefore, clear space can be obtained in real time while the size increase of the apparatus is avoided.

According to the teachings herein, the clear-space-calculating unit calculates clear space through the following mathematical expression:

$$CS = \frac{1}{C_{deq}} \int_0^{te} C_d(t) \cdot Q_d(t) dt \qquad [\text{Math. 3}]$$

(where CS denotes clear space, Cdeq denotes the equilibrium value stored in the storage unit, Cd(t) denotes the concentration of the predetermined substance detected by the concentration-detecting unit, Qd(t) denotes dialysate flow rate, t denotes arbitrary time in the blood purification treatment, and te denotes the end time of the blood purification treatment). Therefore, clear space can be calculated correctly and easily with the concentration-detecting unit, which detects the concentration of the predetermined substance in the waste dialysate.

According to the teachings herein, the control unit establishes the state of equilibrium by reducing or stopping the dialysate flow rate, increasing the blood flow rate, or causing the dialysate to circulate through the blood purifier. Thus, a state of equilibrium can be established simply and easily.

According to the teachings herein, the concentration-detecting unit includes the light-emitting portion that emits light toward the waste dialysate, the light-receiving portion that receives the light emitted from the light-emitting portion and transmitted through the waste dialysate, and the detecting portion that detects the absorbance in accordance with the intensity of the light received by the light-receiving portion. Furthermore, the concentration-detecting unit detects the concentration of the predetermined substance in the waste dialysate in accordance with the absorbance detected by the detecting portion. Therefore, the concentration of the predetermined substance in the waste dialysate can be detected accurately without bringing the waste dialysate or the blood into contact with any sensor or the like.

According to the teachings herein, the storage unit stores the absorbance detected by the detecting portion in the state of equilibrium as an equilibrium value. Furthermore, the clear-space-calculating unit calculates clear space in accordance with the absorbance detected by the detecting portion and the equilibrium value stored in the storage unit. Therefore, clear space can be obtained in real time by utilizing the ratio of the absorbance that correlates with the ratio of the concentration of the predetermined substance.

According to the teachings herein, the clear-space-calculating unit calculates clear space through the following mathematical expression:

$$CS = \frac{1}{\text{Abs}_{eq}} \int_0^{te} \text{Abs}(t) \cdot Q_d(t) dt \qquad [\text{Math. 4}]$$

(where CS denotes clear space, Abs denotes the absorbance detected by the detecting portion, Abseq denotes the equilibrium value stored in the storage unit, Qd(t) denotes dialysate flow rate, t denotes arbitrary time in the blood purification treatment, and te denotes the end time of the blood purification treatment). Therefore, clear space can be calculated correctly and easily by utilizing the ratio of the absorbance that correlates with the ratio of the concentration of the predetermined substance.

According to the teachings herein, the blood purification apparatus includes the total-body-fluid-volume-calculating unit that calculates the patient's total body-fluid volume in accordance with the clear space calculated by the clear-space-calculating unit. Therefore, calculating the clear space makes it possible to calculate the patient's total body-fluid volume more correctly and in real time.

DETAILED DESCRIPTION

Embodiments of the present invention will now be described specifically with reference to the drawings.

Figure 1:
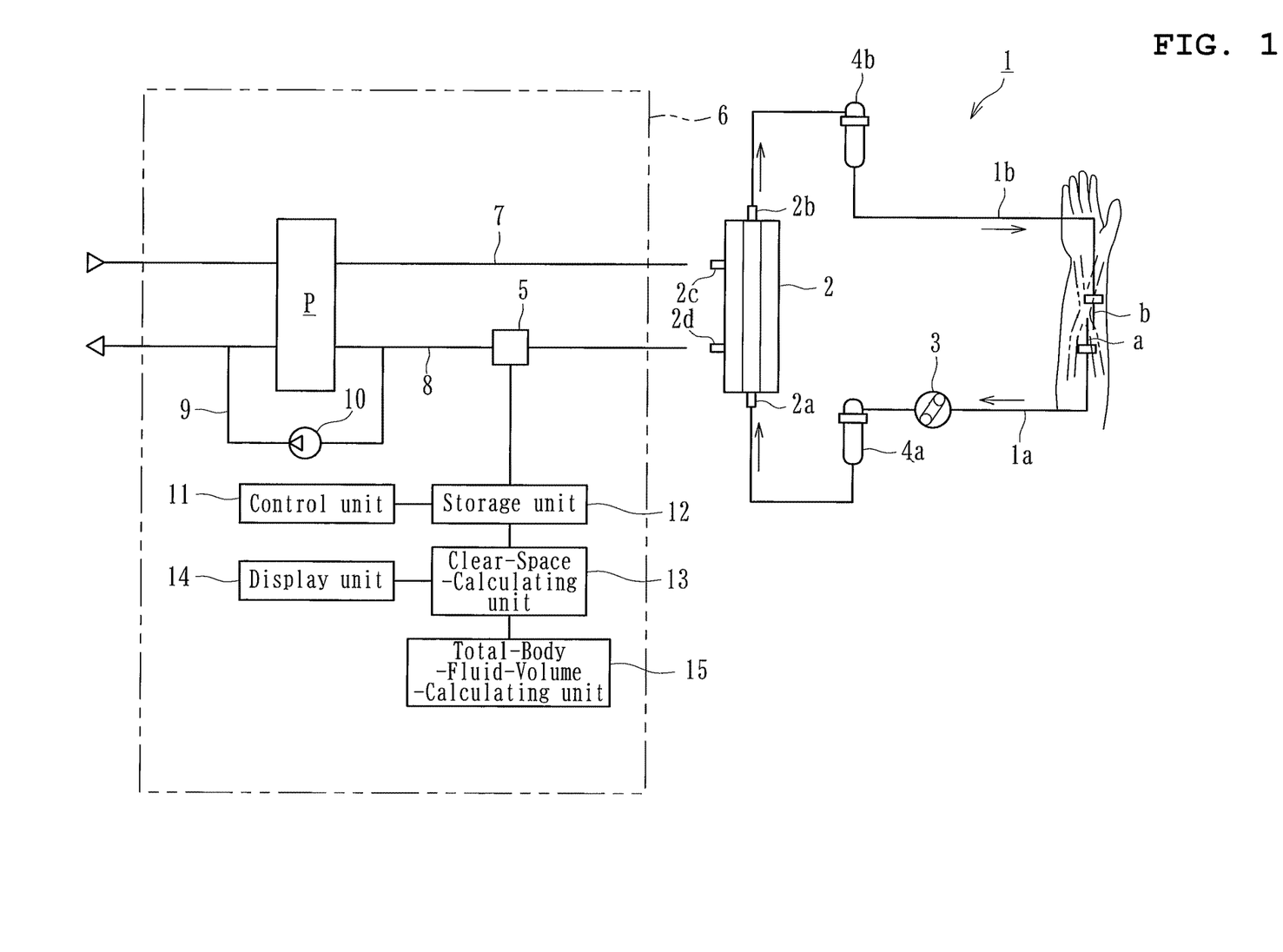
FIG. 1 is a diagram of a blood purification apparatus according to an embodiment of the present invention.

A blood purification apparatus according to an embodiment is provided for purifying a patient's blood while causing the blood to extracorporeally circulate, and is applied to a hemodialysis apparatus intended for hemodialysis treatment. As illustrated in FIG. 1, the hemodialysis apparatus basically includes a blood circuit 1 that causes the patient's blood to extracorporeally circulate, a dialyzer 2 as a blood purifier, a waste-liquid-concentration sensor 5 as a concentration-detecting unit, and a dialysis device 6 that performs ultrafiltration while supplying dialysate to the dialyzer 2. The dialysis device 6 includes a dialysate introduction line 7 and a dialysate drain line 8, a control unit 11, a storage unit 12, a clear-space-calculating unit 13, and a total-body-fluid-volume-calculating unit 15.

As illustrated in the drawing, the blood circuit 1 basically includes an arterial blood circuit 1a and a venous blood circuit 1b each formed of a flexible tube. The dialyzer 2 is connected between the arterial blood circuit 1a and the venous blood circuit 1b. The arterial blood circuit 1a is provided with an arterial (blood-removal or blood-collection) puncture needle a at a distal end thereof and with a peristaltic blood pump 3 and an air-trap chamber 4a for bubble removal at respective halfway positions thereof. The venous blood circuit 1b is provided with a venous (blood-return) puncture needle b at a distal end thereof and with an air-trap chamber 4b for bubble removal at a halfway position thereof.

When the blood pump 3 is activated while the patient is punctured with the arterial puncture needle a and the venous puncture needle b, the patient's blood flows through the arterial blood circuit 1a while undergoing bubble removal in the air-trap chamber 4a, and reaches the dialyzer 2, where the blood is purified and ultrafiltered. Then, the blood flows through the venous blood circuit 1b while undergoing bubble removal in the air-trap chamber 4b, and returns into the patient's body. Thus, the patient's blood is purified by the dialyzer 2 while being caused to extracorporeally circulate through the blood circuit 1. In this specification, the side of the puncture needle provided for blood removal (blood collection) is referred to as the "arterial" side, and the side of the puncture needle provided for blood return is referred to as the "venous" side. The "arterial" side and the "venous" side are not defined in accordance with which of the artery and the vein is to be the object of puncture.

The dialyzer 2 (the blood purifier) has, in a housing thereof, a blood introduction port 2a, a blood delivery port 2b, a dialysate introduction port 2c, and a dialysate delivery port 2d. The blood introduction port 2a is connected to a proximal end of the arterial blood circuit 1a. The blood delivery port 2b is connected to a proximal end of the venous blood circuit 1b. The dialysate introduction port 2c and the dialysate delivery port 2d are connected to distal ends of the dialysate introduction line 7 and the dialysate drain line 8, respectively, extending from the dialysis device 6.

The dialyzer 2 houses a plurality of hollow fibers. The inside of each of the hollow fibers serves as a blood flow route. The space between the outer peripheral surface of each of the hollow fibers and the inner peripheral surface of the housing serves as a dialysate flow route. The hollow fibers each have a number of very small holes (pores) extending therethrough from the outer peripheral surface to the inner peripheral surface, thereby forming a hollow fiber membrane. Waste matter, excessive water, and the like contained in the blood permeate through the membranes into the dialysate.

The dialysis device 6 includes a duplex pump P, a bypass line 9 connected to the dialysate drain line 8 in such a manner as to bypass a drain-side pump chamber of the duplex pump P, and an ultrafiltration pump 10 connected to the bypass line 9. The duplex pump P is provided over the dialysate introduction line 7 and the dialysate drain line 8. The duplex pump P introduces the dialysate into the dialyzer 2 through the dialysate introduction line 7 and drains the dialysate in the dialyzer 2, together with the waste matter in the blood, through the dialysate drain line 8. The duplex pump P may be replaced with another device (such as a device employing a so-called balancing chamber or the like).

One end of the dialysate introduction line 7 is connected to the dialyzer 2 (the dialysate introduction port 2c), and the other end is connected to a dialysate supply device (not illustrated) that prepares a dialysate at a predetermined concentration. One end of the dialysate drain line 8 is connected to the dialyzer 2 (the dialysate delivery port 2d), and the other end is connected to a drainage unit (not illustrated). Hence, the dialysate introduction line 7 allows the dialysate supplied from the dialysate supply device to be introduced into the dialyzer 2, while the dialysate drain line 8 allows waste dialysate resulting from the blood purification performed by the dialyzer 2 to be drained from the dialyzer 2 to the drainage unit.

The ultrafiltration pump 10 is provided for removing water (excessive water) from the patient's blood flowing through the dialyzer 2. Specifically, when the ultrafiltration pump 10 is activated, the volume of liquid drained through the dialysate drain line 8 exceeds the volume of dialysate introduced through the dialysate introduction line 7. Hence, water is removed from the blood by a volume corresponding to the excess.

Figure 2:
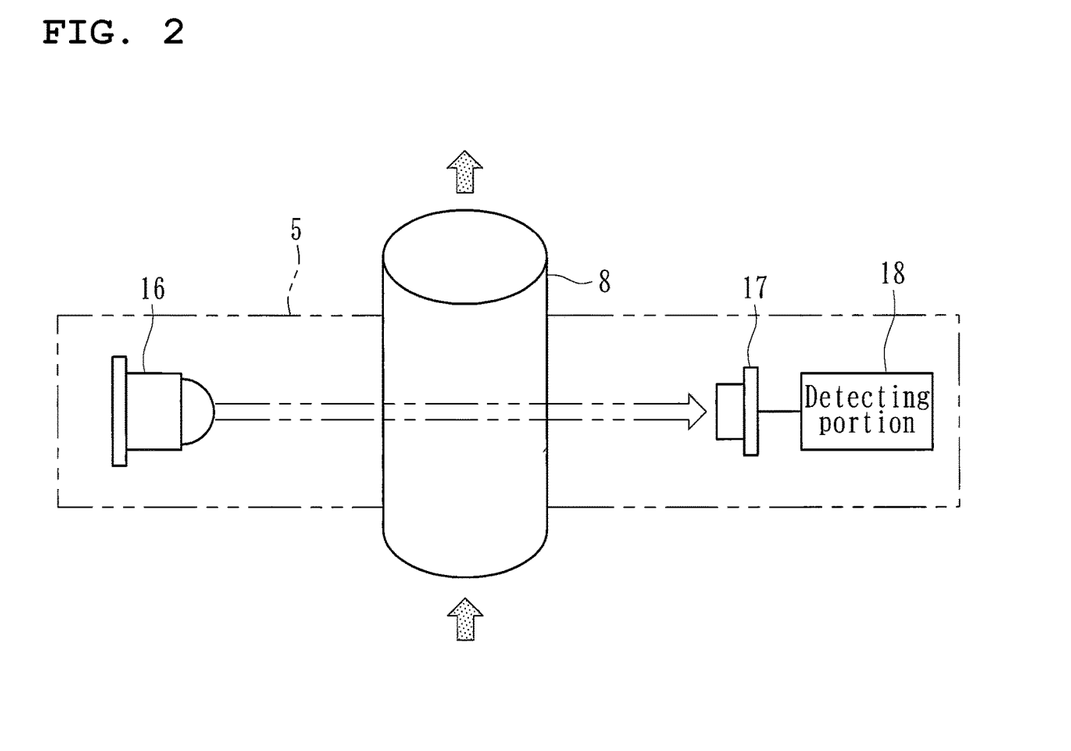
FIG. 2 is a diagram of a concentration-detecting unit included in the blood purification apparatus.

The waste-liquid-concentration sensor 5 (the concentration-detecting unit) is provided on the dialysate drain line 8 in the dialysis device 6 and detects the concentration of a predetermined substance (for example, the concentration of a substance such as urea or uric acid contained in the waste dialysate) contained in the liquid (in the present embodiment, the waste dialysate drained from the dialyzer 2 as the blood purifier) that flows with the blood purification performed by the dialyzer 2. As illustrated in FIG. 2, the waste-liquid-concentration sensor 5 basically includes a light-emitting portion 16, a light-receiving portion 17, and a detecting portion 18. The light-emitting portion 16 and the light-receiving portion 17 are positioned across the dialysate drain line 8 from each other.

The light-emitting portion 16 is a light source such as an LED and emits light (ultraviolet light (UV)) to the liquid (in the present embodiment, the waste dialysate drained from the dialyzer 2). The light transmitted through the liquid is received by the light-receiving portion 17. The light-receiving portion 17 according to the present embodiment is a light-receiving device capable of generating a voltage corresponding to the intensity of the light received. The detecting portion 18 detects the concentration of the waste dialysate in accordance with the voltage corresponding to the intensity of the received light. The detecting portion 18 detects absorbance in accordance with the intensity of the light received by the light-receiving portion 17, and thus detects the concentration of the predetermined substance in the waste dialysate (the concentration of urea or the like) in accordance with the absorbance.

Specifically, when light is emitted from the light-emitting portion 16 while the waste dialysate is flowing through the dialysate drain line 8, the light is transmitted through the waste dialysate flowing through the dialysate drain line 8. The light is absorbed by an amount corresponding to the concentration of the waste dialysate, and is eventually received by the light-receiving portion 17. Then, a signal representing the intensity of the light received by the light-receiving portion 17 (i.e., the voltage generated in correspondence with the intensity of the received light) is transmitted to the detecting portion 18, where the absorbance is calculated in accordance with the light intensity measured. Thus, the concentration of the waste dialysate flowing through the dialysate drain line 8 is obtained.

The waste-liquid-concentration sensor 5 according to the present embodiment is an optical sensor including the light-emitting portion 16 that emits ultraviolet light (UV) at a wavelength of about 300 nm (280 to 320 nm). Alternatively, the waste-liquid-concentration sensor 5 may be an optical sensor that emits another kind of light such as infrared light, or an enzyme sensor or the like instead of an optical sensor. While the waste-liquid-concentration sensor 5 according to the present embodiment is provided at a position of the dialysate drain line 8 on the upstream side with respect to the duplex pump P (on the side connected to the dialyzer 2), the waste-liquid-concentration sensor 5 may be provided on the downstream side with respect to the duplex pump P.

Figure 4:
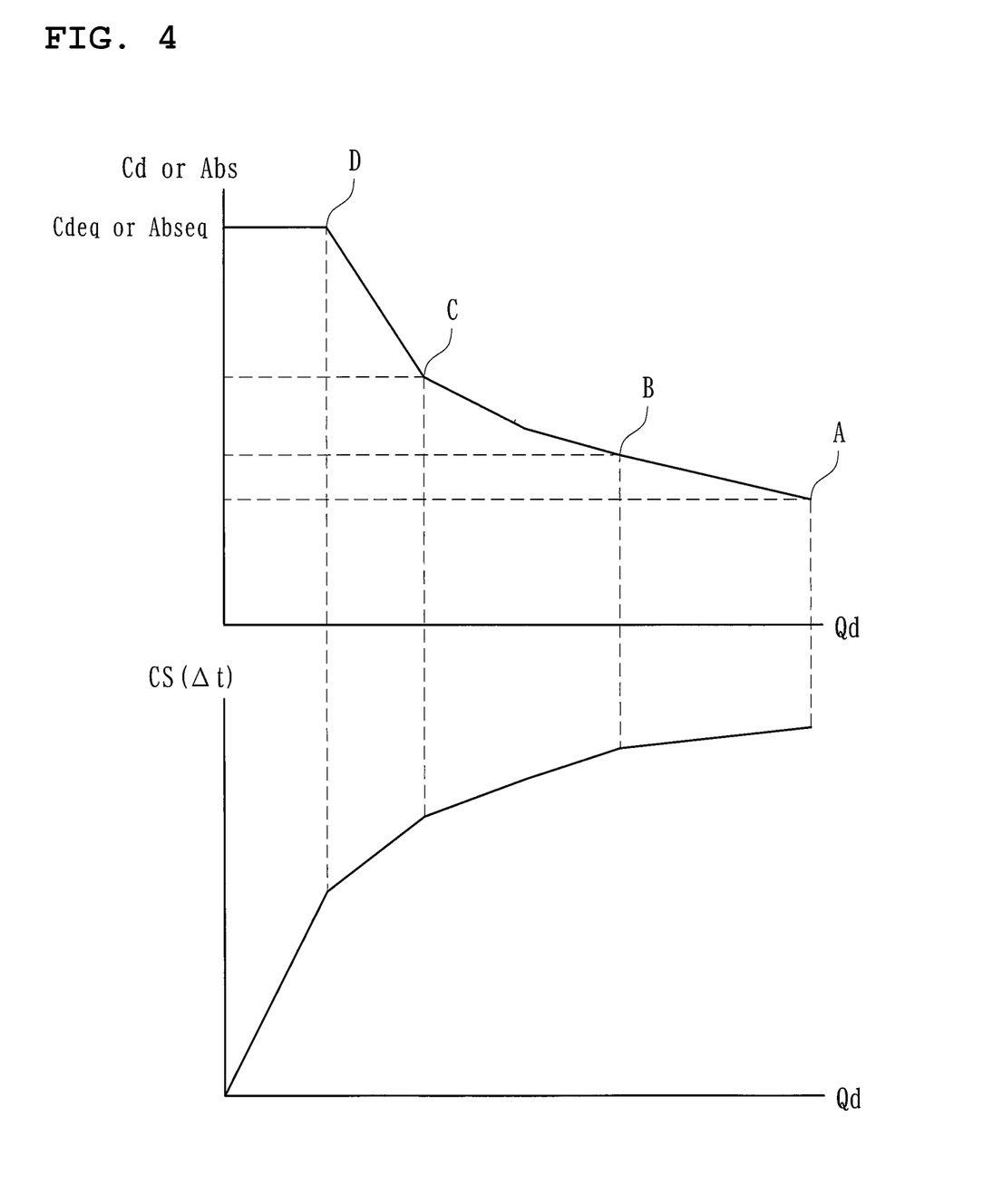
FIG. 4 includes a graph illustrating, with an equilibrium value (Cdeq or Abseq), a relationship between dialysate flow rate (Qd) and a detected value (Cd or Abs) observed in a process of establishing a state of equilibrium by the blood purification apparatus (a process of reducing the dialysate flow rate), and a graph illustrating a corresponding relationship between dialysate flow rate), and a graph illustrating a corresponding relationship between dialysate flow rate (Qd) and clear space per time (CS(Δt)).

The control unit 11 is a microcomputer or the like provided in the dialysis device 6 and establishes a state of equilibrium where the concentration of the predetermined substance (the concentration of the waste matter such as urea) in the waste dialysate flowing through the dialysate drain line 8 and the concentration of the predetermined substance (the concentration of the waste matter such as urea) in the blood flowing through the blood circuit 1 (at the inlet of the dialyzer 2) are equal or approximate to each other. Specifically, as illustrated in FIG. 4, while the dialysate flow rate (Qd) is reduced gradually, the concentration (Cd) or the absorbance (Abs) is detected at each of points A to D by the waste-liquid-concentration sensor 5, whereby a graph representing a relationship between the dialysate flow rate (Qd) and the concentration (Cd) or the absorbance (Abs) can be obtained. The state where the concentration of the predetermined substance in the waste dialysate flowing through the dialysate drain line 8 and the concentration of the predetermined substance in the blood flowing through the blood circuit 1 are approximate to each other indicates that the ratio between the two concentrations falls within a range of 0.7 to 1.3. The ratio between the two concentrations is preferably within a range of 0.8 to 1.2, more preferably within a range of 0.9 to 1.1.

In such a state, even if the dialysate flow rate (Qd) is reduced from the point D, the concentration (Cd) or the absorbance (Abs) remains constant (such a constant value is referred to as equilibrium value (equilibrium concentration Cdeq or equilibrium absorbance Abseq)). Therefore, it is understood that a "state of equilibrium" has been established where the concentration of the predetermined substance (the concentration of the waste matter such as urea) in the waste dialysate flowing through the dialysate drain line 8 and the concentration of the predetermined substance (the concentration of the waste matter such as urea) in the blood flowing through the blood circuit 1 are equal or approximate to each other.

The storage unit 12 is electrically connected to the control unit 11 and to the waste-liquid-concentration sensor 5 and stores, as an "equilibrium value", the value detected by the waste-liquid-concentration sensor 5 (the concentration-detecting unit) in the state of equilibrium (i.e., the concentration (Cdeq) of the predetermined substance or the absorbance (Abseq) observed in the state of equilibrium). That is, the control unit 11 establishes a state of equilibrium, and the value detected by the waste-liquid-concentration sensor 5 in the state of equilibrium is stored in the storage unit 12 as an equilibrium value (an equilibrium concentration (Cdeq) or an equilibrium absorbance (Abseq)).

The clear-space-calculating unit 13 calculates "clear space (CS)" in accordance with the value detected by the waste-liquid-concentration sensor 5 and the equilibrium value (the equilibrium concentration (Cdeq) or the equilibrium absorbance (Abseq)) stored in the storage unit 12. Clear space (CS) is an index representing the volume of purification of the patient achieved by the blood purification treatment. The clear-space-calculating unit 13 according to the present embodiment obtains the clear space (CS) as follows.

First, clearance (CL) as a figure of merit representing the degree of solute removal by the dialyzer 2 will be discussed. Clearance (CL) is a function defined by blood flow rate (Qb), dialysate flow rate (Qd), and overall mass transfer coefficient ($K_0A$) alone. It is known that when the dialysate flow rate (Qd) is small enough with respect to the blood flow rate (Qb) and the overall mass transfer coefficient ($K_0A$), the dialysate flow rate (Qd) serves as the rate-determining factor, which establishes CL=Qd, regardless of the blood flow rate (Qb) and the overall mass transfer coefficient ($K_0A$) (see the following, for example: Akihiro Yamashita, "Basics of Blood Purification: The Japanese Journal of Clinical Dialysis", 1999, Vol. 15, No. 8, pp. 101-105).

Assuming that the amount of adsorption to the purification membranes in the dialyzer 2 is 0, blood-concentration-based clearance (CLb) based on blood concentration and waste-liquid-concentration-based clearance (CLd) based on waste-dialysate concentration are the same (indicate the same context). In such a case, clearance CL (CLb and CLd) can be obtained as the product of the ratio between the concentration (Cd) of the predetermined substance (urea) in the waste dialysate and the concentration (Cbi) of the predetermined substance (urea) at the inlet of the dialyzer 2 in the blood circuit 1, and the dialysate flow rate (Qd) (i.e., CL=(Cd/Cbi)×Qd Expression (a)) (see the following, for example: Michio Mineshima, "Performance and Evaluation of Dialyzer", "Clinical Engineering", 2011, Vol. 22, No. 5, pp. 407-411).

When dialysate flow rate (Qd) is the rate-determining factor, clearance (CL) is equal to dialysate flow rate (Qd), as described above. Hence, Expression (b) given below can be obtained through Expression (a), and Expression (c) can be obtained through Expression (b). Note that "Cdeq" denotes the concentration of the predetermined substance (urea) in the waste dialysate when the dialysate flow rate (Qd) is reduced enough to be the rate-determining factor.

$$CL/Qd=Cdeq/Cbi=1 \qquad \text{Expression (b)}$$

$$Cbi=Cdeq \qquad \text{Expression (c)}$$

If the above state of equilibrium is established immediately after the blood purification treatment (immediately after starting the dialysis), the equilibrium value Cdeq(0) at the beginning of the treatment becomes equal or approximate to the initial concentration Cb(0) of the predetermined substance for the patient (i.e., the concentration of the predetermined substance in the patient's body). Therefore, Expression (d) below holds.

$$Cb(0)=Cdeq(0) \quad \text{Expression (d)}$$

Furthermore, removal volume (M) of the predetermined substance can be obtained by graphically integrating Qd×Cd (t) that is measured over time. Therefore, Expression (e) below holds. Note that "t" denotes arbitrary time in the blood purification treatment, and "te" denotes the end time of the blood purification treatment.

[Math. 5]

$$M=\int_0^{te} C_d(t) \cdot Q_d(t) dt \quad \text{Expression (e)}$$

Furthermore, clear space (CS) can be obtained by standardizing the removal volume (M) with Cb(0) (see the following, for example: Akihiro Yamashita, "Basics of Blood Purification: The Japanese Journal of Clinical Dialysis", 1999, Vol. 15, No. 12, pp. 113-118). Therefore, Expression (f) below holds.

$$CS=M/Cb(0) \quad \text{Expression (f)}$$

Here, it is understood that substituting the relationships of Expression (d) and Expression (e) into Expression (f) yields Expression (g), given below, to be used for calculating clear space (CS). That is, clear space (CS) can be obtained through a multiplication of the ratio of the concentration (Cd) of the predetermined substance by dialysate flow rate (Qd).

[Math. 6]

$$CS = \frac{1}{C_{deq(0)}} \int_0^{te} C_d(t) \cdot Q_d(t) dt \quad \text{Expression (g)}$$

To summarize, the clear-space-calculating unit 13 according to the present embodiment is capable of calculating clear space through the following mathematical expression (Expression (g)):

$$CS = \frac{1}{C_{deq(0)}} \int_0^{te} C_d(t) \cdot Q_d(t) dt \quad \text{[Math. 7]}$$

(where CS denotes clear space, Cdeq denotes the equilibrium value stored in the storage unit, Cd(t) denotes the concentration of the predetermined substance detected by the concentration-detecting unit, Qd(t) denotes dialysate flow rate, and te denotes the end time of the blood purification treatment). The clear space (CS) calculated as above can be obtained continuously with no correction, even if any change is made in treatment conditions such as blood flow rate and dialysate flow rate.

Furthermore, it is known that there is a correlation between the ratio (Cd/Cdeq) of the concentration (Cd) of the predetermined substance and the ratio (Abs/Abseq) of the absorbance (Abs) at the waste-liquid-concentration sensor 5 (the concentration-detecting unit) (see the following, for example: F. Uhlin, I. Fridolin, L. G. Lindberg et al., "Estimation of Delivered Dialysis Dose by On-Line Monitoring of the Ultraviolet Absorbance in the Spent Dialysate", American Journal of Kidney Diseases, 2003, Volume 41, Issue 5, pp. 1026-1036).

Therefore, clear space (CS) can be obtained through Expression (h) below, by replacing the ratio (Cd/Cdeq) of the concentration (Cd) of the predetermined substance in Expression (g) above with the ratio (Abs/Abseq) of the absorbance (Abs).

[Math. 8]

$$CS = \frac{1}{Abs_{eq(0)}} \int_0^{te} Abs(t) \cdot Q_d(t) dt \quad \text{Expression (h)}$$

In such a case, the storage unit 12 stores the absorbance detected by the detecting portion 18 (the concentration-detecting unit) in the state of equilibrium as an equilibrium value (an equilibrium absorbance Abseq), and the clear-space-calculating unit 13 can calculate clear space in accordance with the absorbance (Abs) detected by the detecting portion 18 and the equilibrium value (Abseq) stored in the storage unit 12.

The clear-space-calculating unit 13 in the above case is capable of calculating clear space through the following mathematical expression (Expression (g)):

$$CS = \frac{1}{Abs_{eq(0)}} \int_0^{te} Abs(t) \cdot Q_d(t) dt \quad \text{[Math. 9]}$$

(where CS denotes clear space, Abs denotes the absorbance detected by the detecting portion, Abseq denotes the equilibrium value stored in the storage unit, Qd(t) denotes dialysate flow rate, and te denotes the end time of the blood purification treatment). The clear space (CS) calculated as above can be obtained continuously with no correction, even if any change is made in treatment conditions such as blood flow rate and dialysate flow rate.

A display unit 14 displays the clear space (CS) calculated by the clear-space-calculating unit 13 and is, for example, a display screen of the dialysis device 6, or a monitor or the like connected to the dialysis device 6. Since the clear space (CS) calculated by the clear-space-calculating unit 13 is displayed by the display unit 14, medical workers including doctors can grasp the clear space accurately. Therefore, the blood purification treatment (dialysis treatment) can be performed smoothly.

Figure 6:
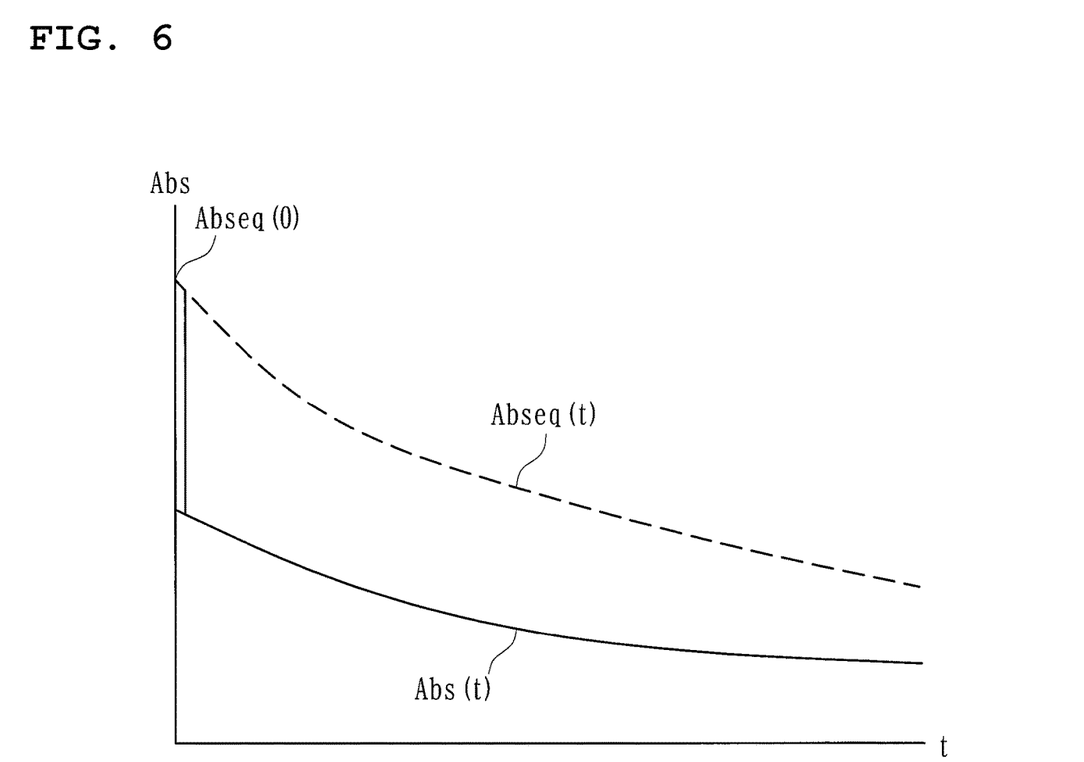
FIG. 6 is a graph illustrating the value (Abs) detected by the concentration-detecting unit (a solid line) and the equilibrium value (Abseq) (a broken line) that change with time.

When the blood purification treatment progresses and the concentration (Cb) of the predetermined substance in the blood flowing through the blood circuit 1 changes (i.e., when the concentration is reduced with time), the absorbance (Abs) as the value detected by the detecting portion 18 of the waste-liquid-concentration sensor 5 changes (decreases) as illustrated by the solid line in FIG. 6. Meanwhile, the equilibrium value (the equilibrium absorbance Abseq) also changes (decreases) as illustrated by the broken line in the drawing. Such changes also apply to the concentration (Cd) of the predetermined substance detected by the waste-liquid-concentration sensor 5.

The total-body-fluid-volume-calculating unit 15 calculates the patient's total body-fluid volume (the total body-fluid volume V(te) at the end of the blood purification treatment) in accordance with the clear space (CS) calculated by the clear-space-calculating unit 13. Specifically, the total body-fluid volume (V) can be obtained through mathematical expressions given below.

As represented by Expression (i) given below, removal rate (Rc) based on the concentration of the predetermined substance can be obtained from concentrations (Cb) of the predetermined substance in the blood that are observed before and after the blood purification treatment (the dialysis treatment) (see the following, for example: Akihiro Yamashita, "Basics of Blood Purification: The Japanese Journal of Clinical Dialysis", 1999, Vol. 15, No. 11, pp. 75-79).

$$Rc=(Cb(0)-Cb(t))/Cb(0) \quad \text{Expression (i)}$$

Furthermore, it is known that there is a correlation between the rate of change in the concentration (Cb) of the predetermined substance in the blood and the rate of change in the concentration (Cd) of the predetermined substance detected by the waste-liquid-concentration sensor 5 (see the following, for example: F. Uhlin, I. Fridolin, L. G Lindberg et al., "Estimation of Delivered Dialysis Dose by On-Line Monitoring of the Ultraviolet Absorbance in the Spent Dialysate", American Journal of Kidney Diseases, 2003, Volume 41, Issue 5, pp. 1026-1036). Therefore, as represented by Expression (j) below, Rc can be obtained from Cd.

$$Rc=(Cd(0)-Cd(t))/Cd(0) \quad \text{Expression (j)}$$

On the other hand, as represented by Expression (k) below, it is known that clear space (CS) can be obtained from removal rate (Rc), body-fluid volume (Vte) at the end of the blood purification treatment, and ultrafiltration volume ($\Delta V$) (see the following, for example: Akihiro Yamashita, "Basics of Blood Purification: The Japanese Journal of Clinical Dialysis", 1999, Vol. 15, No. 12, pp. 113-118).

$$CS=Rc \times V(te)+\Delta V \quad \text{Expression (k)}$$

According to Expression (j) and Expression (k), the patient's total body-fluid volume (Vte) observed after the blood purification treatment can be calculated as follows.

$$CS(te)=(Cd(0)-Cd(t))/Cd(0) \times V(te)+\Delta V$$

$$V(te)=(CS(te)-\Delta V(te))/(1-Cd(te)/Cd(0)) \quad \text{Expression (l)}$$

As described above, the ratio between Cb and Cd correlates with the ratio of the absorbance (Abs) detected by the waste-liquid-concentration sensor 5 (the concentration-detecting unit). Therefore, as represented by Expression (m) below, the patient's total body-fluid volume V(te) observed after the blood purification treatment can be obtained through a combination with the ratio of Abs.

$$V(te)=(CS(te)-\Delta V(te))/(1-Abs(te)/Abs(0)) \quad \text{Expression (m)}$$

To summarize, the total-body-fluid-volume-calculating unit 15 is capable of calculating the patient's total body-fluid volume (the patient's total body-fluid volume observed after the blood purification treatment) through the mathematical expression (Expression (l) above) $V(te)=(CS(te)-\Delta V(te))/(1-Cd(te)/Cd(0))$ or the mathematical expression (Expression (m) above) $V(te)=(CS(te)-\Delta V(te))/(1-Abs(te)/Abs(0))$. If (te) denoting the time in the blood purification treatment is replaced with the current time (t) in the treatment, the patient's total body-fluid volume at the current time can be obtained.

Figure 3:
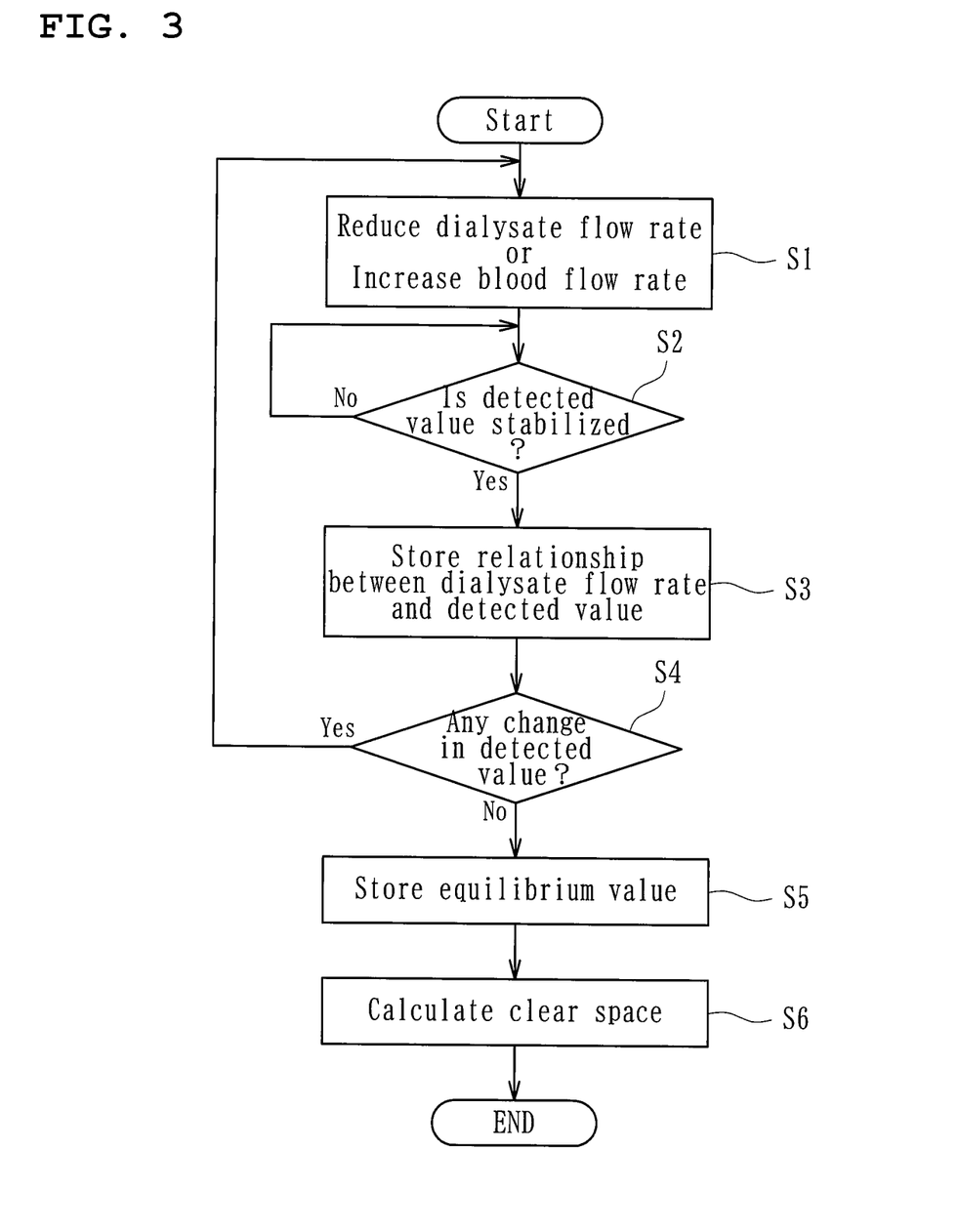
FIG. 3 is a flow chart illustrating a control process undergone by the blood purification apparatus.

Now, a process of calculating clear space that is undergone by the blood purification apparatus according to the present embodiment will be described with reference to the flow chart illustrated in FIG. 3.

First, the blood pump 3 and the duplex pump P are activated while the patient is punctured with the arterial puncture needle a and the venous puncture needle b, whereby blood is caused to flow into the blood circuit 1 through the dialyzer 2 while dialysate is caused to flow through the dialysate introduction line 7 and the dialysate drain line 8. In the above state, in step S1, the dialysate flow rate (Qd) is reduced by a predetermined value. Then, in step S2, the process is stopped until the value (the concentration Cd of the predetermined substance or the absorbance (Abs)) detected by the waste-liquid-concentration sensor 5 (the concentration-detecting unit) is stabilized. When the value is judged to be stabilized, the process proceeds to step S3, where the relationship between the dialysate flow rate (Qd) and the detected value (the concentration Cd of the predetermined substance or the absorbance (Abs)) is stored in the storage unit 12.

Then, in step S4, whether there is any change greater than or equal to a predetermined threshold in the value detected by the waste-liquid-concentration sensor 5 (the concentration-detecting unit) is checked. If there is a change greater than or equal to the predetermined threshold, the process returns to step S1, where the dialysate flow rate (Qd) is reduced by a predetermined value. Furthermore, steps S2 to S4 are performed sequentially. If it is judged in step S4 that there is no change greater than or equal to the predetermined threshold in the value detected by the waste-liquid-concentration sensor 5 (the concentration-detecting unit) (i.e., if the detected value is judged to be constant), the process proceeds to step S5, where the detected value is stored as an equilibrium value (an equilibrium concentration (Cdeq) or an equilibrium absorbance (Abseq)) in the storage unit 12.

Specifically, as illustrated in FIG. 4, when the dialysate flow rate (Qd) is sequentially reduced from point A to point D and is further reduced from point D, the value (the concentration (Cd) of the predetermined substance or the absorbance (Abs)) detected by the waste-liquid-concentration sensor 5 (the concentration-detecting unit) becomes constant, establishing a "state of equilibrium". Therefore, the value detected in the state of equilibrium (at point D) is stored as an equilibrium value (an equilibrium concentration (Cdeq) or an equilibrium absorbance (Abseq).

Then, the process proceeds to step S6, where the clear-space-calculating unit 13 calculates clear space (CS) through the following mathematical expression:

$$CS = \frac{1}{C_{deq(0)}} \int_0^{te} C_d(t) \cdot Q_d(t) dt \quad \text{[Math. 10]}$$

(where CS denotes clear space, Cdeq denotes the equilibrium value stored in the storage unit, Cd(t) denotes the concentration of the predetermined substance detected by the concentration-detecting unit, Qd(t) denotes dialysate flow rate, and te denotes the end time of the blood purification treatment), or through the following mathematical expression:

$$CS = \frac{1}{Abs_{eq(0)}} \int_0^{te} Abs(t) \cdot Q_d(t) dt \quad \text{[Math. 11]}$$

(where CS denotes clear space, Abs denotes the absorbance detected by the detecting portion, Abseq denotes the equilibrium value stored in the storage unit, Qd(t) denotes dialysate flow rate, and te denotes the end time of the blood purification treatment).

When the clear space (CS) is obtained in step S6, as illustrated in FIG. 4, the storage unit 12 can store not only the equilibrium value (Cdeq or Abseq) and the relationship between the dialysate flow rate (Qd) and the value (Cd or Abs) detected by the waste-liquid-concentration sensor 5 (the concentration-detecting unit) (see the upper graph in the drawing) but also the relationship between the dialysate flow rate (Qd) and the clear space (CS) (see the lower graph in the drawing).

According to the present embodiment, a state of equilibrium is established by reducing the dialysate flow rate (Qd). Alternatively, a state of equilibrium may be established by increasing the blood flow rate (Qb). In the latter case, in step S1, the blood flow rate (Qb) is increased by a predetermined value. Subsequently, in step S2, the process is stopped until the value (the concentration Cd of the predetermined substance or the absorbance (Abs)) detected by the waste-liquid-concentration sensor 5 (the concentration-detecting unit) is stabilized. Then, when the value is judged to be stabilized, the process proceeds to step S3, where the relationship between the blood flow rate (Qb) and the detected value (the concentration Cd of the predetermined substance or the absorbance (Abs)) is stored in the storage unit 12.

Figure 5:
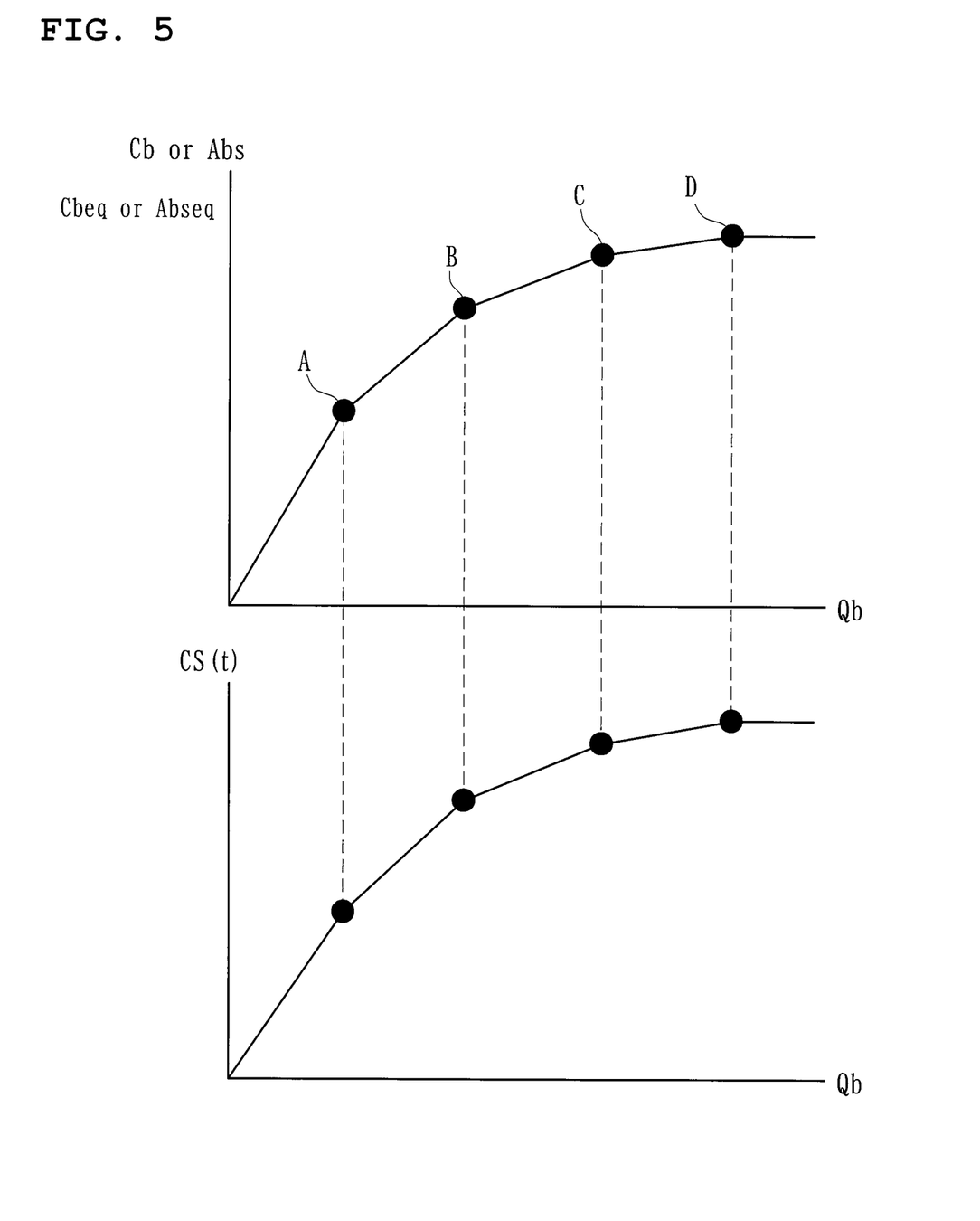
FIG. 5 includes a graph illustrating, with an equilibrium value (Cbeq or Abseq), a relationship between blood flow rate (Qb) and a detected value (Cb or Abs) observed in a process of establishing a state of equilibrium by the blood purification apparatus (a process of increasing the blood flow rate), and a graph illustrating a corresponding relationship between blood flow rate (Qb) and clear space per time (CS(Δt)).

Specifically, as illustrated in FIG. 5, when the blood flow rate (Qb) is sequentially increased from point A to point D and is further increased from point D, the value (the concentration (Cd) of the predetermined substance or the absorbance (Abs)) detected by the waste-liquid-concentration sensor 5 (the concentration-detecting unit) becomes constant, establishing a "state of equilibrium". Therefore, the value detected in the state of equilibrium (at point D) is stored as an equilibrium value (an equilibrium concentration (Cdeq) or an equilibrium absorbance (Abseq).

The control unit 11 according to the present embodiment establishes a "state of equilibrium" by reducing the dialysate flow rate (Qd) or increasing the blood flow rate (Qb) as described above. Alternatively, a state of equilibrium may be established by setting the dialysate flow rate (Qd) to 0 (stopping the supply of the dialysate) or causing the dialysate to circulate through the dialyzer 2 (the blood purifier). As described above, the control unit 11 establishes a state of equilibrium by reducing or stopping the dialysate flow rate (Qd), increasing the blood flow rate (Qb), or causing the dialysate to circulate through the dialyzer 2. Thus, a state of equilibrium can be established simply and easily.

According to the above embodiment, a state of equilibrium is established where the concentration of the predetermined substance in the waste dialysate flowing through the dialysate drain line 8 and the concentration of the predetermined substance in the blood flowing through the blood circuit 1 are equal or approximate to each other. Furthermore, the value detected by the waste-liquid-concentration sensor 5 (the concentration-detecting unit) in the state of equilibrium is stored as an equilibrium value. Furthermore, clear space (CS) as an index representing the volume of purification of the patient achieved by the blood purification treatment is calculated in accordance with the value detected by the waste-liquid-concentration sensor 5 and the equilibrium value stored in the storage unit 12. Therefore, clear space (CS) can be obtained in real time while the size increase of the apparatus is avoided.

Furthermore, the clear-space-calculating unit 13 according to the present embodiment calculates clear space through the following mathematical expression:

$$CS = \frac{1}{C_{deq(0)}} \int_0^{te} C_d(t) \cdot Q_d(t) dt \qquad \text{[Math. 12]}$$

(where CS denotes clear space, Cdeq denotes the equilibrium value stored in the storage unit, Cd(t) denotes the concentration of the predetermined substance detected by the concentration-detecting unit, Qd(t) denotes dialysate flow rate, and te denotes the end time of the blood purification treatment). Therefore, clear space can be calculated correctly and easily with the waste-liquid-concentration sensor 5, which detects the concentration of the predetermined substance in the waste dialysate.

Furthermore, the waste-liquid-concentration sensor 5 (the concentration-detecting unit) according to the present embodiment includes the light-emitting portion 16 that emits light toward the waste dialysate, the light-receiving portion 17 that receives the light emitted from the light-emitting portion 16 and transmitted through the waste dialysate, and the detecting portion 18 that detects the absorbance in accordance with the intensity of the light received by the light-receiving portion 17. Furthermore, the waste-liquid-concentration sensor 5 detects the concentration of the predetermined substance in the waste dialysate in accordance with the absorbance detected by the detecting portion 18. Therefore, the concentration of the predetermined substance in the waste dialysate can be detected accurately without bringing the waste dialysate into contact with any sensor or the like.

According to the present embodiment, the storage unit 12 stores the absorbance detected by the detecting portion 18 in the state of equilibrium as an equilibrium value (Abseq). Furthermore, the clear-space-calculating unit 13 calculates clear space in accordance with the absorbance (Abs) detected by the detecting portion 18 and the equilibrium value (Abseq) stored in the storage unit 12. Therefore, clear space can be obtained in real time by utilizing the ratio of the absorbance that correlates with the ratio of the concentration of the predetermined substance.

In particular, the clear-space-calculating unit 13 according to the present embodiment calculates clear space through the following mathematical expression:

$$CS = \frac{1}{Abs_{eq(0)}} \int_0^{te} Abs(t) \cdot Q_d(t) dt \qquad \text{[Math. 13]}$$

(where CS denotes clear space, Abs denotes the absorbance detected by the detecting portion, Abseq denotes the equilibrium value stored in the storage unit, Qd(t) denotes dialysate flow rate, and te denotes the end time of the blood purification treatment). Therefore, clear space can be calculated correctly and easily by utilizing the ratio of the absorbance that correlates with the ratio of the concentration of the predetermined substance.

Furthermore, the blood purification apparatus includes the total-body-fluid-volume-calculating unit 15 that calculates the patient's total body-fluid volume in accordance with the clear space (CS) calculated by the clear-space-calculating unit 13. Therefore, calculating the clear space makes it possible to calculate the patient's total body-fluid volume more correctly and in real time. Typically, the patient's total body-fluid volume is estimated to be about several tens of percent (for example, about 60%) of the patient's weight. Compared with such a case, according to the present embodiment, the patient's total body-fluid volume can be calculated accurately and in real time in accordance with the clear space calculated by the clear-space-calculating unit 13.

While the present embodiment has been described above, the present invention is not limited thereto. For example, the value detected by the waste-liquid-concentration sensor 5 (the concentration-detecting unit) and the equilibrium value that are to be used for calculating the clear space may be replaced with other parameters, as long as such parameters each correlate with the concentration of the predetermined substance. For example, factors such as the voltage or the current outputted by the waste-liquid-concentration sensor 5 may be employed in addition to the absorbance. Moreover, the mathematical expressions for calculating clear space by the clear-space-calculating unit 13 are not limited to those given above, and may be other mathematical expressions.

While the present embodiment concerns a case where the calculated clear space is displayed on the display unit 14, the calculated clear space may be informed to medical workers including doctors through another device such as a speaker. Alternatively, instead of providing or displaying such information, the clear space calculated by the clear-space-calculating unit 13 may be, for example, exclusively used for internal processing performed for making settings of the treatment. While the present embodiment is applied to a hemodialysis apparatus, the present invention may also be applied to a blood purification apparatus intended for another treatment (such as hemofiltration treatment or hemodiafiltration treatment) for purifying blood while causing the blood to extracorporeally circulate.

The present invention is applicable to any blood purification apparatus, including those having other additional functions, as long as the apparatus includes a control unit that establishes a state of equilibrium where the concentration of a predetermined substance in waste dialysate flowing through a dialysate drain line and the concentration of the predetermined substance in blood flowing through a blood circuit are equal or approximate to each other, a storage unit that stores a value detected by a concentration-detecting unit in the state of equilibrium as an equilibrium value, and a clear-space-calculating unit that calculates clear space in accordance with the value detected by the concentration-detecting unit and the equilibrium value stored in the storage unit, the clear space being an index representing the volume of purification of a patient achieved by blood purification treatment.

REFERENCE SIGN LIST 1 blood circuit
1a arterial blood circuit
1b venous blood circuit
2 dialyzer (blood purifier)
3 blood pump
4a, 4b air-trap chamber
5 waste-liquid-concentration sensor (concentration-detecting unit)
6 dialysis device
7 dialysate introduction line
8 dialysate drain line
9 bypass line
10 ultrafiltration pump
11 control unit
12 storage unit
13 clear-space-calculating unit
14 display unit
15 total-body-fluid-volume-calculating unit
16 light-emitting portion
17 light-receiving portion
18 detecting portion
P duplex pump

The invention claimed is:

1. A blood purification apparatus to which a blood circuit that allows a patient's blood to extracorporeally circulate and a blood purifier connected to the blood circuit and that purifies the blood in extracorporeal circulation are attachable, the blood purification apparatus including
a dialysate introduction line through which dialysate is introduced into the blood purifier;
a dialysate drain line through which waste dialysate resulting from blood purification performed by the blood purifier is drained from the blood purifier; and
a concentration-detecting unit that detects a concentration of a predetermined substance in the waste dialysate flowing through the dialysate drain line, the blood purification apparatus comprising:
a control unit that establishes a state of equilibrium where the concentration of the predetermined substance in the waste dialysate flowing through the dialysate drain line and a concentration of the predetermined substance in the blood flowing through the blood circuit are equal or approximate to each other;
a storage unit that stores a value detected by the concentration-detecting unit in the state of equilibrium as an equilibrium value; and
a clear-space-calculating unit that calculates clear space in accordance with the value detected by the concentration-detecting unit and the equilibrium value stored in the storage unit, the clear space being an index representing a volume of purification of a patient achieved by blood purification treatment; and
wherein the control unit establishes a state of equilibrium by changing a dialysate flow rate through the dialysate drain line or a blood flow rate through the blood circuit until the change in the value detected by the concentration-detecting unit becomes less than a predetermined threshold.

2. The blood purification apparatus according to claim 1, wherein the clear-space-calculating unit calculates clear space through the following mathematical expression:

$$CS = \frac{1}{C_{deq(0)}} \int_0^{te} C_d(t) \cdot Q_d(t) dt \qquad [\text{Math. 1}]$$

(where CS denotes clear space, Cdeq denotes the equilibrium value stored in the storage unit, Cd(t) denotes the concentration of the predetermined substance detected by the concentration-detecting unit, Qd(t) denotes dialysate flow rate, t denotes arbitrary time in the blood purification treatment, and te denotes end time of the blood purification treatment).

3. The blood purification apparatus according to claim 1, wherein the control unit establishes the state of equilibrium by reducing or stopping a dialysate flow rate, increasing a blood flow rate, or causing the dialysate to circulate through the blood purifier.

4. The blood purification apparatus according to claim 1, wherein the concentration-detecting unit includes a light-emitting portion that emits light toward the waste dialysate, a light-receiving portion that receives the light emitted from the light-emitting portion and transmitted through the waste dialysate, and a detecting portion that detects absorbance in accordance with an intensity of the light received by the light-receiving portion, the concentration-detecting unit detecting the concentration of the predetermined substance in the waste dialysate in accordance with the absorbance detected by the detecting portion.

5. The blood purification apparatus according to claim 4, wherein the storage unit stores, as the equilibrium value, the absorbance detected by the detecting portion in the state of equilibrium, and the clear-space-calculating unit calculates clear space in accordance with the absorbance detected by the detecting portion and the equilibrium value stored in the storage unit.

6. The blood purification apparatus according to claim 5, wherein the clear-space-calculating unit calculates clear space through the following mathematical expression $$CS = \frac{1}{\text{Abs}_{eq(0)}} \int_0^{te} \text{Abs}(t) \cdot Q_d(t) dt \qquad \text{[Math. 2]}$$

(where CS denotes clear space, Abs denotes the absorbance detected by the detecting portion, Abseq denotes the equilibrium value stored in the storage unit, Qd(t) denotes dialysate flow rate, t denotes arbitrary time in the blood purification treatment, and te denotes end time of the blood purification treatment).

7. The blood purification apparatus according to claim 1, further comprising a total-body-fluid-volume-calculating unit that calculates a patient's total body-fluid volume in accordance with the clear space calculated by the clear-space-calculating unit.

8. The blood purification apparatus according to claim 1, to which the blood circuit and the blood purifier are attached.

9. A blood purification apparatus to which a blood circuit that allows a patient's blood to extracorporeally circulate and a blood purifier connected to the blood circuit and that purifies the blood in extracorporeal circulation are attachable, the blood purification apparatus including:

a dialysate introduction line through which dialysate is introduced into the blood purifier;
a dialysate drain line through which waste dialysate resulting from blood purification performed by the blood purifier is drained from the blood purifier; and
a concentration-detecting unit that detects a concentration of a predetermined substance in the waste dialysate flowing through the dialysate drain line, the blood purification apparatus comprising:
a control unit that establishes a state of equilibrium where the concentration of the predetermined substance in the waste dialysate flowing through the dialysate drain line and a concentration of the predetermined substance in the blood flowing through the blood circuit are equal or approximate to each other;
a storage unit that stores a value detected by the concentration-detecting unit in the state of equilibrium as an equilibrium value; and
a clear-space-calculating unit that calculates clear space in accordance with the value detected by the concentration-detecting unit and the equilibrium value stored in the storage unit, the clear space being an index representing a volume of purification of a patient achieved by blood purification treatment;
wherein the control unit establishes the state of equilibrium by reducing or stopping a dialysate flow rate, increasing a blood flow rate, or causing the dialysate to circulate through the blood purifier; and
wherein the control unit stops the dialysate flow rate or circulates the dialysate through the blood purifier to establish a state of equilibrium in which the change in the value detected by the concentration-detecting unit becomes less than a predetermined threshold.

* * * * *